United States Patent [19]

Wilson et al.

[11] Patent Number: 5,280,787
[45] Date of Patent: Jan. 25, 1994

[54] ULTRASONIC METHOD AND APPARAUS FOR DETERMINATION OF VESSEL LOCATION AND SIZE

[75] Inventors: Laurence S. Wilson, Allambie Heights; Michael J. Dadd, Lane Cove; Robert W. Gill, Rozelle, all of Australia

[73] Assignee: Commonwealth Scientific and Industrial Research Organisation, Campbell, Australia

[21] Appl. No.: 915,841

[22] PCT Filed: Jan. 24, 1991

[86] PCT No.: PCT/AU91/00026

§ 371 Date: Sep. 16, 1992

§ 102(e) Date: Sep. 16, 1992

[87] PCT Pub. No.: WO91/11146

PCT Pub. Date: Aug. 8, 1991

[30] Foreign Application Priority Data

Jan. 25, 1990 [AU] Australia .................... PJ8331/90

[51] Int. Cl.⁵ .................... A61B 8/00; A61B 8/06
[52] U.S. Cl. .................... 128/661.1; 128/660.05
[58] Field of Search .................... 128/660.04–660.05, 128/662.07–661.10, 662.04, 662.06

[56] References Cited

U.S. PATENT DOCUMENTS

| | | | |
|---|---|---|---|
| 4,873,985 | 10/1989 | Nakajima | 128/661.1 X |
| 4,913,159 | 4/1990 | Gardin et al. | 128/661.1 |
| 5,078,148 | 1/1992 | Nassi et al. | 128/661.1 X |
| 5,195,521 | 3/1993 | Melton, Jr. et al. | 128/661.1 X |

*Primary Examiner*—Francis Jaworski
*Attorney, Agent, or Firm*—Ladas & Parry

[57] ABSTRACT

An improved technique for establishing the position, dimensions and orientation of a vessel which is essentially free of internal acoustic discontinuities involves scanning the vessel with a beam of ultrasonic energy and, from the ultrasonic echoes received in the A-mode lines of sight of the ultrasonic beam, establishing a B-mode image of the vessel. An angle marker, in the form of a short line segment, is established, using the B-mode image, on or near a straight axis of the vessel. The length of the angle marker is divided into a number of sub-sectors, each of which receives approximately the same number of A-mode lines of sight of the ultrasonic beam. An average A-mode signal is obtained for each sub-sector. Comparison of the average A-mode signals provides information about the orientation of the angle marker relative to the axis of the vessel. Combining the average A-mode signals to obtain a composite signal and performing edge-detection analysis of the composite signal enables the edges of the vessel to be established with precision, and the diameter of the vessel to be determined accurately. A single computer can programmed to perform the analysis and re-position the angle markers (if necessary) on to the axis of the vessel. Using information obtained from this technique, accurate values of the flow rate of a fluid moving within the vessel can be obtained when Doppler frequency shift measurements are made.

15 Claims, 4 Drawing Sheets

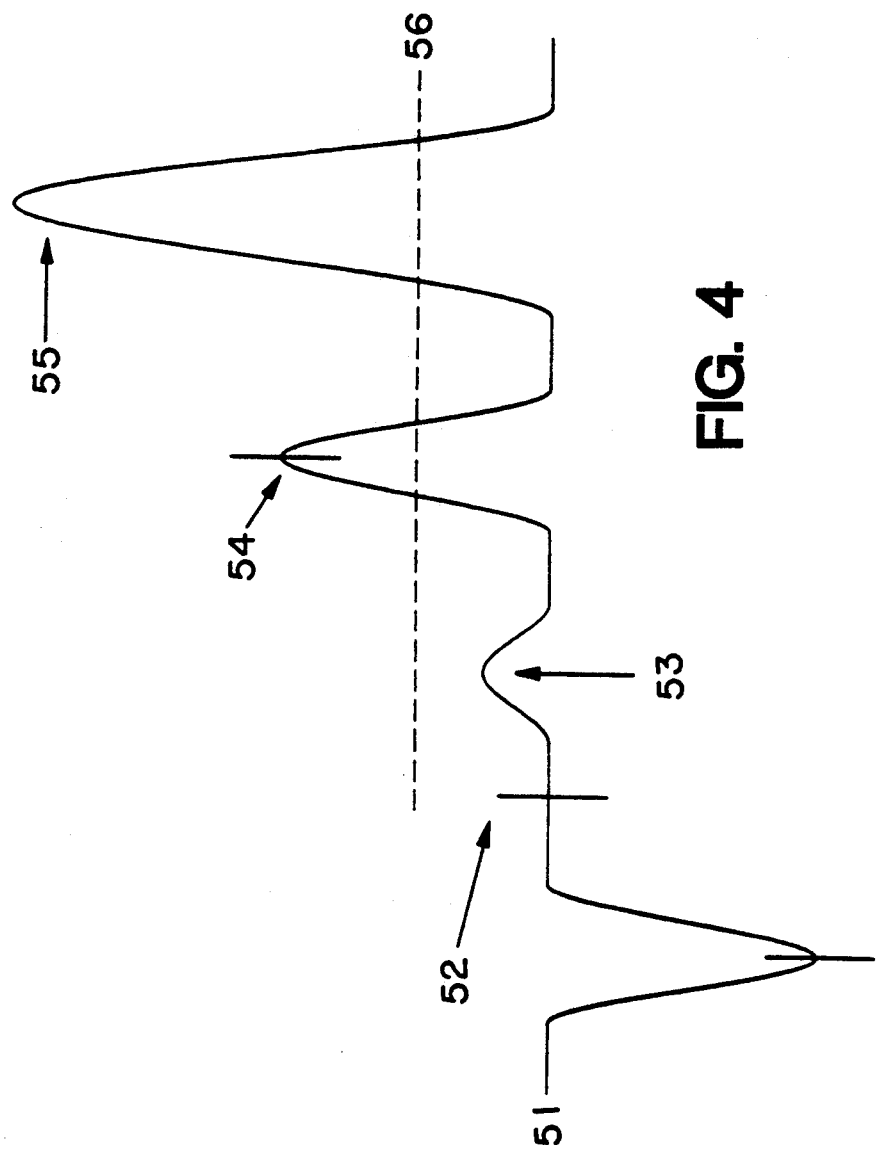

ULTRASONIC METHOD AND APPARAUS FOR DETERMINATION OF VESSEL LOCATION AND SIZE

TECHNICAL FIELD

This invention relates to the measurement of the size and orientation of hidden vessels, such as the vessels in the human body through which blood flows, using ultrasonic echoscopy. It has particular application to the measurement of the flow of blood in blood vessels using the Doppler frequency shift in conjunction with ultrasonic measurement techniques, but it is not limited to blood flow measurement. The present invention provides a method for improving the current ultrasonic techniques for measuring the size and orientation of vessels, and hence for obtaining measurements of the flow through such vessels.

BACKGROUND

It is now well known that ultrasonic echoscopy techniques can be used to provide information about an object that is not visible to the eye. The basic technique of ultrasonic echoscopy involves directing a short pulse of ultrasonic energy, typically in the frequency range from 1 MHz to 30 MHz, into the region of the object that is being examined, and observing the energy that is reflected, as an echo, from each acoustic impedance discontinuity in that region. Each echo received is converted into an electrical signal and displayed as either a blip or an intensified spot on a single trace of a cathode ray tube or television screen. Such a display of the echoes is known as an "A-mode" echograph or echogram, and is useful in a number of diagnostic techniques to locate the boundaries of the object or to provide other information about the region into which the pulse of ultrasonic energy has been directed.

If a series of adjacent A-mode displays are obtained (for example, by physically or electrically moving the transmitting transducer which produces the pulses of ultrasonic energy, or by scanning the direction of transmission of the pulses of ultrasonic energy), a two-dimensional image of the object under examination may be displayed on the cathode ray tube or television screen. Such an image or display of acoustic discontinuities is known as a "B-mode" image or display.

The use of the Doppler frequency shift in the ultrasonic examination of flowing liquids and moving objects is also well known. Many echoscopes which perform the B-mode imaging examination described above can also perform Doppler frequency shift measurements in respect of echoes returned from moving objects within the region receiving ultrasonic energy from the echoscope When the object under examination is a blood vessel, measurement of the Doppler shift of echoes from the blood cells within the vessel permits the velocity of those blood cells to be estimated. As pointed out by R W Gill, in his article entitled "Measurement of Blood Flow by Ultrasound: Accuracy and Sources of Error", which was published in *Ultrasound in Medicine and Biology*, Volume 11 (1985), pages 625 to 641, it is possible to measure the total volume of flow per unit time using an ultrasonic examination technique which includes the measurement of frequency changes due to the Doppler effect.

In ultrasonic examinations including Doppler frequency shift measurements, it is necessary to obtain echoes from a limited volume of the flowing liquid which is within the vessel being examined. This is achieved by fixing the line of sight of the ultrasonic transducer and, in the most commonly used version of Doppler measurement known as "pulsed Doppler", analysing the echoes obtained from the sample volume for a limited range of time delays. The Doppler shift in the received echoes is averaged in order to calculate the average speed of scatterers in the flowing liquid.

In current applications of the pulsed Doppler technique, a small sample volume within the vessel is selected by the operator of the echoscope, who moves a graphical representation of the sample volume over a B-mode image of the vessel. In this way, the B-mode imaging equipment is used to steer the ultrasonic beam and adjust the sample volume delay so that the actual sample volume position corresponds to that part of the vessel which is to be the subject of the Doppler shift measurement. The orientation of the vessel has to be known, so that the velocity of the liquid within the vessel may be calculated from the well-known Doppler equation:

$$v = \frac{f_D \cdot c}{2 \cdot f_0 \cdot \cos \theta} \quad (1)$$

where $f_D$ is the Doppler shift frequency, $f_0$ is the transmitted frequency, v is the blood velocity, c is the speed of sound and $\theta$ is the angle between the line of sight of the ultrasonic beam and the direction of flow of the liquid. In current implementations of this technique, the orientation of the vessel is obtained from observations of the graphical representation of the sample volume in the B-mode ultrasonic image.

In the volumetric measurement of flow, a larger sample volume is placed to encompass the entire vessel, and the total flow is calculated using the relationship:

$$\text{flow} = \frac{f_D \cdot c \cdot \pi \cdot d^2}{2 \cdot f_0 \cdot \cos \theta \cdot 4} \quad (2)$$

where d is the vessel diameter and $f_D$ is the mean Doppler shift in frequency. When applying this formula, the diameter of the vessel is estimated by the operator, who identifies the positions of the two internal vessel walls on the B-mode image and places cursors on their images. The diameter of the vessel is taken as the distance between the cursor positions. This is a difficult measurement, and because the flow is directly proportional to the square of the diameter in the expression for flow, errors in the diameter measurement translate into greater errors when the flow values are estimated.

Another factor affecting the accuracy of blood flow measurements is the fact that, in humans and animals, the diameter of most vessels varies during the cardiac cycle. This is particularly so in the case of arteries. Hence, for greatest accuracy, the instantaneous values of $f_D$ and d should be obtained repeatedly and the expression in equation (2) should be averaged over several cardiac cycles.

DISCLOSURE OF THE PRESENT INVENTION

It is an object of the present invention to provide an improved ultrasonic echoscopy method and apparatus in which the following three pieces of information may be obtained in real time:

(a) vessel location for accurate placement of the sample volume;

(b) vessel orientation (for the "cos θ" factor correction if liquid flow measurements are to be made); and (c) vessel diameter (for volumetric flow measurements).

Preferably, utilising the present invention, the measurement process can be repeated frequently if any of these parameters are likely to change with movement (for example, in the cardiac cycle).

Automatic adjustment of the position of the sample volume in ultrasonic echoscopy has been demonstrated previously. One technique for doing this is described in the paper by J G Davis, K L Richards and D Greene entitled "A sample volume tracking unit for pulsed Doppler echocardiography", which was published in *IEEE Transactions on Biomedical Engineering*, volume BME-26 (1979) pages 285–288. However, that technique uses a single line of sight and thus is capable of axial shifts only. That and similar prior art techniques do not recognise actual structures associated with the surrounding tissues, nor do they permit measurement of the vessel orientation and diameter.

The present invention achieves computational efficiency by using one-dimensional signal processing techniques. It makes use of two-dimensional data from a selected number of adjacent A-mode ultrasonic lines of sight in a given B-mode image frame and iterates using data from successive images. It uses echoes obtained while the echoscope is in its imaging mode, and makes use of the facts that (i) images of vessels containing a fluid (for example, blood vessels) are normally free of internal echoes, and (ii) the vessels on which Doppler studies are carried out, or in respect of which other measurements are likely to be taken, are normally locally straight.

According to the present invention, there is provided a method of establishing the dimensions and orientation of a vessel which, when subjected to ultrasonic echoscopy examination, is found to be essentially free of substantial internal acoustic discontinuities, said vessel having an axis which is straight in at least part of the vessel, said method comprising the steps of (a) obtaining a B-mode ultrasonic echogram image of said vessel or the part thereof in which said axis is straight from a number of A-mode ultrasonic images, each corresponding to a respective A-mode line of sight of a beam of ultrasonic energy which is scanned over said vessel or said part thereof;

(b) establishing an angle marker in the form of a short line segment within or close to the B-mode image of said vessel or said part thereof;

(c) establishing a plurality of adjacent sub-sectors within the B-mode echogram image of said vessel or part thereof; each of said sub-sectors being intersected by said angle marker; each sub-sector receiving substantially the same number of adjacent A-mode lines of sight of said scanning beam;

(d) obtaining an average video-detected A-mode signal for each of said sub-sectors, (e) performing a comparison of said average A-mode signals of the sub-sectors and determining from said comparison the difference between the orientation of the axis of said vessel and said angle marker and the orientation of said axis of said vessel;

(f) combining said average A-mode signals to obtain a composite A-mode signal for said vessel or part thereof; and (g) performing edge-detection analysis on said composite A-mode signal, to obtain a value of the diameter of said vessel or part thereof.

This method, it will be apparent, may be combined with the Doppler measurement technique to obtain an accurate measurement of the flow of a liquid within the vessel (for example, the flow of blood in an artery, or through a cardiac vessel).

Preferably, the data obtained from the scanning beam of ultrasonic energy is obtained in digital form, so that the production of the average A-mode signal for each sub-sector, the comparison (typically obtained by signal superimposition) of such average A-mode signals, the difference determinations, the production of a composite A-mode signal, and the edge-detection analysis may be performed using (a) digital computer, appropriately programmed.

The present invention also encompasses apparatus for establishing the orientation and cross-sectional dimensions of a vessel having an axis, said apparatus comprising:

(a) conventional apparatus for generating a beam of ultrasonic energy and scanning said beam over at least part of said vessel, to obtain a B-mode ultrasonic echogram image of said vessel or part thereof from a number of A-mode ultrasonic images, each corresponding to a respective A-mode line of sight of said beam;

(b) operator-activated means for establishing an angle marker in the form of a short line segment within or close to the B-mode image of said vessel or part thereof;

(c) accumulation means for accumulating echoes relating to respective sub-sectors of a plurality of sub-sectors of said B-mode image, said sub-sectors (i) being adjacent to each other, (ii) being intersected by said angle marker, and (iii) containing substantially equal numbers of adjacent A-mode lines of sight of said scanning beam;

(d) averaging means for producing a respective average A-mode signal for each of said sub-sectors;

(e) comparison means for comparing said average A-mode signals and for obtaining differences between the average A-mode signals, to enable the orientation of said axis relative to said angle marker to be computed;

(f) combining means for combining said average A-mode signals to produce a composite A-mode signal; and (g) analytical means to perform edge analysis on said composite A-mode signal and to obtain therefrom a value of the diameter of said vessel or part thereof.

As will be apparent from the comments made above concerning the method of the present invention, Doppler signal-generating and processing equipment may be used in conjunction with this apparatus for establishing the orientation and cross-sectional dimensions of the vessel, to provide apparatus for accurately measuring the flow of liquid within the vessel.

These and other features of the present invention will be demonstrated in the following description of an embodiment of the present invention, which is provided by way of example only. In the following description, reference will be made to the accompanying drawings.

BRIEF DESCRIPTION OF THE DRAWINGS

FIG. 4 shows another waveform and its processing in accordance with the preferred edge detection algorithm.

DETAILED DESCRIPTION OF THE ILLUSTRATED EMBODIMENT

Figure 1:
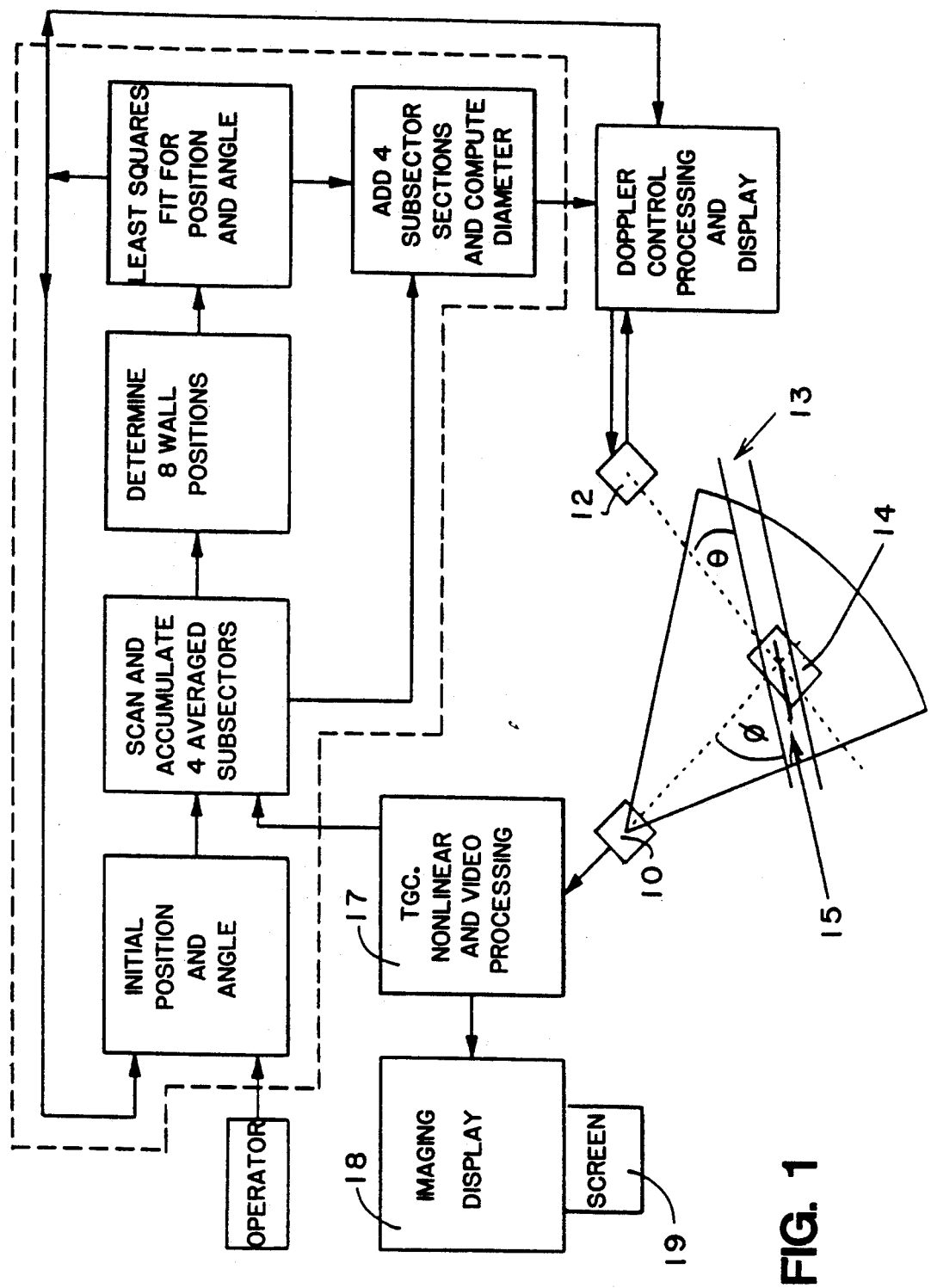
FIG. 1 is a block diagram of a flow measurement system incorporating the present invention and a Doppler frequency shift measurement arrangement, with the ultrasonic beam scanning arrangement indicated schematically thereon.

The apparatus illustrated in FIG. 1 includes a conventional B-mode ultrasonic echograph arrangement comprising an ultrasonic beam generating, beam transmitting and echo receiving transducer 10, which is arranged to scan the ultrasonic beam to and fro through a sector 11. A portion of a tubular vessel 13 (for example, an artery) that is to be investigated is located within the sector 11. Echoes received from acoustic discontinuities in the path of the lines of sight of the scanned ultrasonic beam are processed in a conventional manner by a time gain compensation (TGC) processing unit, non-linear amplification, and video detection stages shown collectively as unit 17 in FIG. 1. The B-mode image of the region of sector 11 is displayed in a conventional manner (on the screen 19 of a television set or cathode ray oscilloscope) by the imaging display unit 18.

A short, linear angle marker is located in the B-mode image of the sector 11 in a location corresponding to the line 15 shown in the sector 11. Thus, effectively, the operator of the apparatus establishes an angle marker 15 within a volume 14 of the vessel that is to be investigated. It will be appreciated that the placing of the angle marker assumes knowledge of the position of the vessel 13. If that knowledge is not available (for example, if the B-mode image is not entirely clear and the vessel 13 cannot be conclusively identified from the image), the angle marker may be placed by an intelligent guess of the location of the vessel 13. Using the present invention, it will be possible to progressively re-position the angle marker by an iterative process until it lies along the axis of the vessel 13. A similar re-positioning of the angle marker will be obtained if the angle marker is initially alongside or intersecting the vessel 13.

Note that the positioning of the angle marker assumes that the vessel 13 is locally straight.

In the illustrated embodiment, as shown in FIG. 2, the portion of the vessel 13 that is being investigated is divided into four sub-sectors, referenced 23, 24, 25 and 26. It will be appreciated, however, that any practical number of sub-sectors may be adopted. Each sub-sector is intersected by the angle marker 15. Each sub-sector is chosen so that it contains substantially the same number of individual A-mode lines of sight of the scanned beam of ultrasonic energy.

The individual A-mode image signals obtained for each of the sub-sectors, in the region where it is expected (or known) that the vessel 13 is located (that is, between the dashed lines 27 and 28 of FIG. 2A, which are parallel to the angle marker line 15), are then accumulated and an average A-mode video image signal is generated for each sub-sector. In FIG. 2, the average A-mode signal for the sub-sector 23, obtained from echoes received from the region between the lines 27 and 28, is shown as waveform 32. The corresponding average A-mode video image signals for the sub-sectors 24, 25 and 26 are shown as signal waveforms 31, 30 and 29, respectively.

Figure 2B:
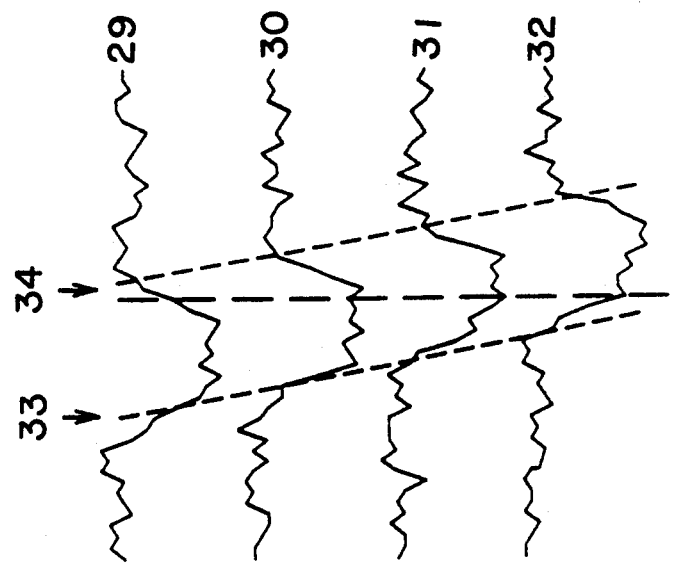
FIGS. 2A and 2B illustrate the creation of sub-sectors and contain representations of the average A-mode signals obtained from the sub-sectors.
Figure 2A:
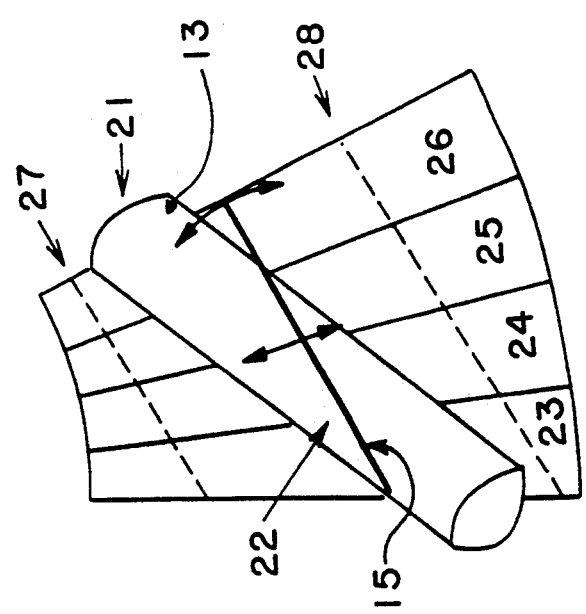

The waveforms 29, 30, 31 and 32 are displayed in FIG. 2B with the axis of the time of arrival of echoes, relative to the intersection of the angle marker 15, horizontal. It will be seen that although (as expected) the waveforms 29, 30, 31 and 32 have similar shapes, they are displaced horizontally and progressively with respect to each other. This apparent offset occurs because the angle marker does not lie parallel to the axis of the vessel 13. The angle that the corresponding points on the displayed waveforms present relative to the angle marker indicates the angle between the angle marker and the axis of the vessel. This angle can be used to determine the orientation of the vessel 13 and/or a new position for the angle marker 15 which is parallel to the axis of the vessel 13.

It will also be apparent that each of the waveforms 29, 30, 31 and 32 contains low-echogenic regions between the (parallel) lines 33 and 34, showing that the region between the lines 33 and 34 is where the vessel is located. The actual position of the intersects between the average A-mode lines of sight signals (assumed to be obtained on the mid-line of each sub-sector) and the vessel walls is then obtained. Preferably this is done using the edge locating algorithm described below with reference to the composite line of sight for the sector. The location of the axis of the vessel 13 relative to the angle marker is then determined (typically obtained by fitting a least squares regression straight line with position along the angle marker as independent variable and deviation of midline position as dependent variable). This information will enable the angle marker to be repositioned on substantially the axis of the vessel before the next measurement of the vessel 13 is undertaken.

Although the information obtained from the waveforms 29, 30, 31 and 32 is adequate to modify the inclination and range of the angle marker, and may be used to estimate the positions of the edges of the vessel 13, the desirability of having a very accurate determination of vessel size means that usually a more detailed analysis is performed to determine the location of the edges of the vessel 13 with precision.

A number of algorithms have been established to determine accurately the actual positions of the walls of the vessel 13. The preferred algorithm, a one-dimensional edge detection method, is described below. As noted above, this algorithm is also the one preferred when determining the orientation of the vessel, using the average A-mode line of sight signals for each sub-sector.

Figure 3:
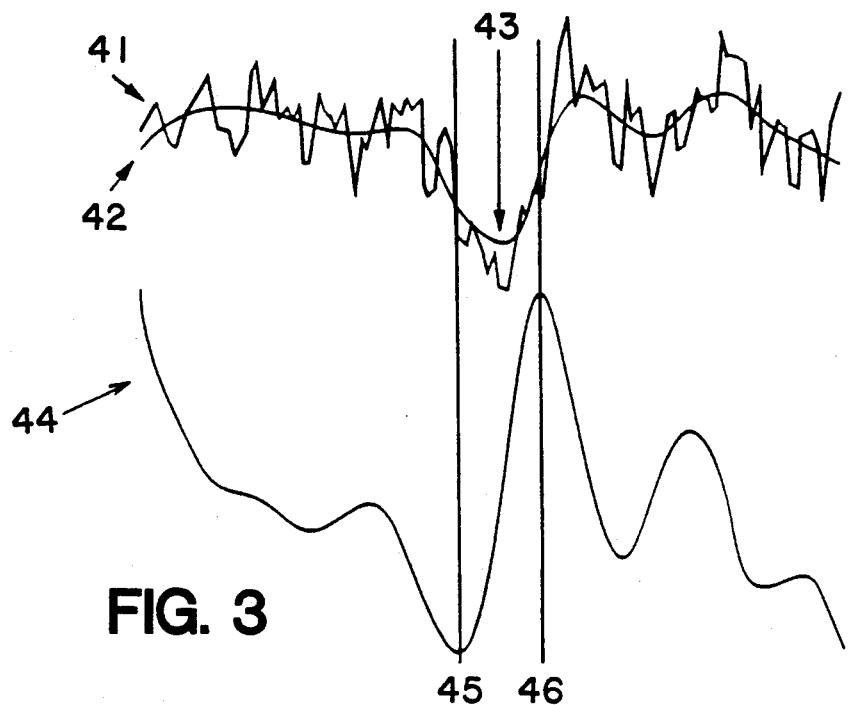
FIG. 3 shows waveforms used in part of the edge detection analysis.

The average A-mode signals for each of the sub-sectors (that is, waveforms 29, 30, 31 and 32) are combined to form a global or composite single A-mode signal, shown as waveform 41 of FIG. 3.

With regard to the generation of the combined (or global, or composite) waveform 41 of FIG. 3, it will be appreciated that if the system illustrated in FIG. 1 is used, it will be necessary to put in a correction factor when combining the average A-mode signals, because they are not parallel to each other. This is preferably done by digitally "re-sampling" the signal waveforms to produce the signal waveforms that would be received if each average A-mode signal was obtained from a beam of ultrasonic energy which crosses the vessel at right angles to the axis of the vessel. It will also be appreciated that if, instead of using an ultrasonic transducer which scans a beam through a sector, a linear array transducer is used, so that all of the A-mode lines of sight of the scanned beam are parallel to each other, a correction will still be required unless the lines of sight intersect the vessel axis at right angles. (When producing the average A-mode signals for each sub-sector, as discussed above, using the equipment of FIG. 1, it is not necessary to compensate for the change in angle, relative to the axis of the vessel, for each line of sight in a sub-sector.

The corrected "raw data" waveform 41 is smoothed using a Gaussian filter (a suitable degree of smoothing corresponds to a Gaussian standard deviation of 1.1 mm) and the resulting smoothed curve 42 is inspected to find its minimum 43. The minimum 43 occurs at the location of the axis of the vessel 13. The smoothed curve 42 is differentiated by the method of first differences and the result (waveform or curve 44) is analysed to detect a minimum 45, which corresponds to the vessel wall nearest to the ultrasonic transducer, and a maximum 47, which corresponds to the vessel wall farthest away from the ultrasonic transducer.

The edge detection algorithm is required to have the further capability of distinguishing the vessel wall from spurious echoes internal to the vessel, or large specular reflectors located outside it. One method of achieving this is as follows.

In FIG. 3, using the position corresponding to the minimum 43 of the smoothed data curve 42 as a starting point, a search is performed in the differentiated data curve 44 for minima closer to the transducer than the starting point, and for maxima further from the transducer than the starting point. Within a certain distance from the starting point (chosen arbitrarily, but realistically, such as 12 mm), the largest nearer local minimum and largest farther local maximum are found. A second search then locates the respective nearer local minimum and farther local maximum nearest the starting point and exceeding a suitable fraction (chosen in the light of experience and typically about 0.25) of the local minimum and maximum found earlier. The nearer local minimum and farther local maximum nearest the starting point, located by this second search, are chosen as the minimum and maximum corresponding the wall positions of the vessel 13.

This selection technique is further illustrated by FIG. 4. In FIG. 4, a plot of the smoothed, differentiated data 51 is shown, with the minimum of the undifferentiated data marked 52. The plot 51 also shows a minimum value and three local maxima 53, 54 and 55, which are candidates for interpretation as the far vessel wall, are shown. After measuring the height of the largest local maximum 55, a threshold level 56 at a suitable fraction (for example, 0.25 of the height of the maximum 55) is established. The local maximum 54 nearest the starting point which exceeds this threshold is taken as the wall position.

After determining the positions of the walls of the vessel 13, the angle marker is normally repositioned to lie substantially along the axis of the vessel, and the measurements are repeated.

FIG. 5 illustrates the circumstances in which movement of the angle marker along its length may be invoked, namely, when the diameter of the vessel, as displayed in the image of the vessel, appears to taper non-linearly. A linear tapering of the vessel presents no problem, but if the image of the vessel tapers non-linearly, this indicates that the image is not entirely along the major axis of the vessel.

Figure 5A:
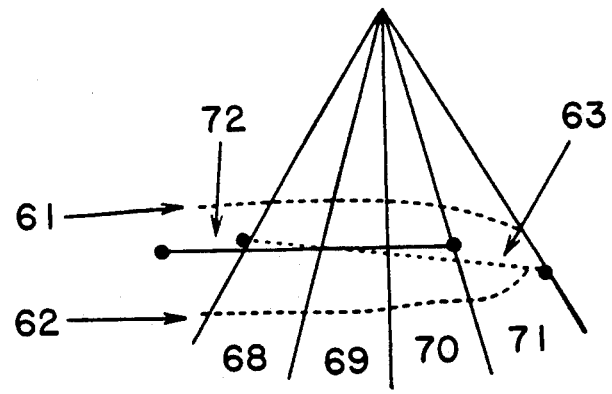
FIGS. 5A and 5B are diagrams which illustrate a situation in which the angle marker will be caused to be displaced along its length.
Figure 5B:
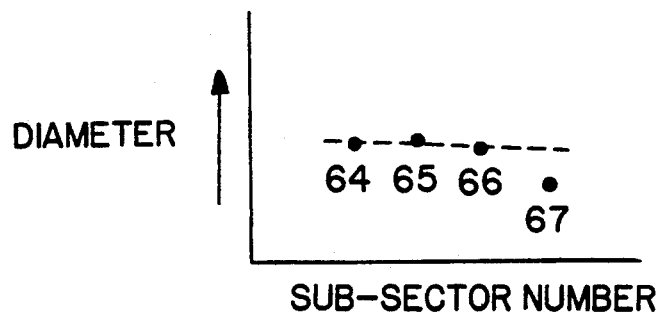

In FIG. 5A, the wall positions 61 and 62 of a vessel have been determined using an angle marker 63 (shown as a dashed line). That the image of the vessel is tapered non-linearly is evident from the diameters 64, 65, 66 and 67, derived from the average A-mode video display signals of the sub-sectors 68, 69, 70 and 71, which have been plotted as part of FIG. 5B, If one of the extreme diameters 64 or 67 is less than a predetermined fraction (such as 0.9) of that predicted by least squares regression on the other three diameters, the angle marker is moved lengthwise to a new position 72 which is substantially on the axis of the vessel, but is farther away from the smallest diameter of the vessel, by a suitable distance (such as one quarter of its length). The length of the angle marker, which defines the length of the region of the vessel 13 that is being investigated, will normally remain constant.

From the foregoing description, it will be seen that, in its implementation, the present invention records and accumulates data from A-mode images obtained using a scanning (that is, an imaging) transducer. Preferably the data is in digital form. This data is recorded after passing through the time gain compensation, non-linear amplification and video detection stages of conventional ultrasound processing. Only A-mode images from lines of sight which pass through the angle marker are required to be recorded. The part of the scanned beam of ultrasonic energy which intersects the angle marker is divided into a number of parts (called "sub-sectors", typically four in number), each containing an approximately equal number of lines of sight of the ultrasonic beam. Within each sub-sector, a sum is formed of all of the lines of sight within that sub-sector to produce a single A-mode video image signal for that sub-sector. In accumulating the summation, the time delay of the beginning of the data from each line of sight is adjusted so that the mid-point of each line of sight coincides with the angle marker, thus taking into account the assumed position and orientation of the vessel.

The accumulated data segment from each sub-sector is analysed using an edge-detection algorithm, to determine the location of the near and far vessel walls at the centre of the sub-sector. The vessel midline or axis is assumed to be halfway between the wall positions determined for each sub-sector, measured along the appropriate line of sight (usually the middle line of sight of each sub-sector). The measured locations for the several midline points (one for each sub-sector) are compared with the location of the angle marker and a least squares fit is used to calculate the error in range and angulation of the vessel relative to the angle marker.

The data segments for each sub-sector are then added together, applying the appropriate correction if the lines of sight do not intersect the vessel at right angles to its axis, and the wall detection algorithm is applied to their sum. The distance between wall positions in this last calculation gives the measured vessel diameter. The errors in range and angulation (determined using the least squares regression method mentioned above) are converted into range and orientation corrections for the angle marker, which are used to establish a new angle marker position. The length of the angle marker remains constant, and its centre normally remains on the same line of sight. However, if the image of the vessel indicates that its diameter tapers non-linearly, the angle marker may be moved lengthwise to its new position.

The new angle marker position is used as input data for the next iteration of the vessel tracking algorithm, which occurs during a subsequent image scan. If the initial angle marker position is greatly in error, several iterations (one per imaging scan) of the algorithm may be necessary to stabilise to the correct value. In a possible implementation, the operator places a single cursor within the vessel of interest, and an angle marker of fixed length and orientation (e.g. horizontal) is generated as the initial angle marker, which iteratively adjusts itself to the true vessel orientation.

Those skilled in the art of ultrasonic echoscopy will recognise that a particular implementation of the invention is in conjunction with the known ultrasonic imaging and pulsed Doppler functions, as shown in FIG. 1. These functions may use the same transducer, different transducers, or different parts of the same transducer where that transducer is of an array type. The imaging transducer may alternate its lines of sight with the Doppler lines of sight, or it may assemble a complete image during a break in the Doppler data acquisition.

The vessel orientation information is supplied to the Doppler module of the machine for substitution in equation 1, and so provide correctly scaled velocities of the liquid in the vessel 13. In machines which measure volumetric flow, the orientation $\theta$ and diameter d are substituted in equation 2 to determine flow. The position of the sample volume is adjusted for subsequent Doppler measurement, and the position and orientation of the angle marker become the input values for the next iteration of the tracking algorithm.

INDUSTRIAL APPLICABILITY

Three particularly useful applications of the present invention are as follows:
(a) In studies of the velocity distribution of blood in vessels over the cardiac cycle, when the sample volume is usually smaller than the vessel, this invention will allow the sample volume to be maintained in a fixed position relative to the (possibly) moving vessel, and will automatically calculate cos $\theta$ for calculating velocity using equation 1.
(b) In volumetric flow studies, when the sample volume is usually larger than the vessel, the invention will enable the sample volume to be maintained in a fixed position relative to the (possibly) moving vessel, and will automatically calculate cos $\theta$ and the vessel diameter d for calculating flow using equation 2.
(c) In Doppler colour flow studies, a two-dimensional image is coloured according to the local velocity of flow, as described by K. Miyatake, M. Okamoto, N. Kinoshita, S. Izumi, M. Owa, S. Takao, H. Sakakibara and Y. Nimura in their article entitled "Clinical applications of a new type of real-time two-dimensional flow imaging system", which was published in *American Journal of Cardiology*, volume 54 (1984), pages 857–868. The present invention will allow the use of equation 1 to correct the displayed velocity so that the displayed velocity is the actual speed of blood along the vessel, rather than the component along the line of sight.

This list of particularly useful applications of the present invention is not intended to be exhaustive.

Finally, it should be noted that although a specific implementation and application of the present invention has been illustrated and described above, the present invention is not limited to that implementation and application. Variations of and modifications to the present invention may be made without departing from the present inventive concept.

We claim:

1. A method of establishing the dimensions and orientation of a vessel which, when subjected to ultrasonic echoscopy examination, is found to be essentially free of substantial internal acoustic discontinuities, said vessel having an axis which is straight in least part of the vessel, said method comprising the steps of
   (a) obtaining a B-mode ultrasonic echogram image of said vessel or the part thereof in which said axis is straight from a number of A-mode ultrasonic images, each corresponding to a respective A-mode line of sight of a beam of ultrasonic energy which is scanned over said vessel or said part thereof;
   (b) establishing an angle marker in the form of a short line segment within or close to the B-mode image of said vessel or said part thereof;
   (c) establishing a plurality of adjacent sub-sectors within the B-mode echogram image of said vessel or part thereof; each of said sub-sectors being intersected by said angle marker; each sub-sector receiving substantially the same number of adjacent A-mode lines of sight of said scanning beam;
   (d) obtaining an average video-detected A-mode signal for each of said sub-sectors,
   (e) performing a comparison of said average A-mode signals of the sub-sectors and determining from said comparison the difference between the orientation of the axis of said vessel and said angle marker and the orientation of said axis of said vessel;
   (f) combining said average A-mode signals to obtain a composite A-mode signal for said vessel or part thereof; and
   (g) performing edge-detection analysis on said composite A-mode signal, to obtain a value of the diameter of said vessel or part thereof.

2. A method as defined in claim 1, in which the step of performing edge-detection analysis includes the sub-steps of
   (i) smoothing the waveform of the composite A-mode signal and identifying a minimum value therein which corresponds to the position of the axis of said vessel;
   (ii) differentiating the smoothed waveform of the composite A-mode signal;
   (iii) identifying a minimum in the differentiated waveform, which occurs between the generation point of the beam of ultrasonic energy and the axis of said vessel and which corresponds to one wall of the vessel and identifying a maximum in the differentiated waveform, farther from generation point of the beam of ultrasonic energy than the axis of said vessel, which corresponds to the other wall of the vessel; and
   (iv) adopting the distance between the minimum identified in step (iii) and the maximum identified in step (iii) as the diameter of the vessel.

3. A method as defined in claim 2, including the additional step of repeating steps (a) to (g) and using the information obtained from step (e) of the last preceding sequence of steps (a) to (g) to perform the step of establishing the angle marker so that the angle marker is positioned substantially on said axis of said vessel.

4. A method as defined in claim 3, in which, when step (e) provides information showing that the B-mode image of said vessel indicates that said vessel is non-linearly tapered in diameter over at least one of said sub-sectors, in the next repeat of said sequence of steps (a) to (g), the establishment of the angle marker is effected so that the angle marker is effectively moved generally lengthwise of its last preceding position.

5. A method as defined in claim 4, in which said B-mode image is displayed on a screen of a television set or cathode ray oscilloscope.

6. A method as defined in claim 4, including the additional step of performing a Doppler frequency shift measurement in respect of fluid flowing through said vessel, and using the established orientation and cross-sectional dimensions of said vessel to calculate the flow rate of said fluid.

7. A method as defined in claim 1 or claim 2, including the additional step of repeating steps (a) to (g) and using the information obtained from step (e) of the last preceding sequence of steps (a) to (g) to perform the step of establishing the angle marker so that the angle marker is positioned substantially on said axis of said vessel.

8. A method as defined in claim 7, in which, when step (e) provides information showing that the B-mode image of said vessel indicates that said vessel is non-linearly tapered in diameter over at least one of said sub-sectors, in the next repeat of said sequence of steps (a) to (g), the establishment of the angle marker is effected so that the angle marker is effectively moved generally lengthwise of its last preceding position.

9. A method as defined in claim 1, in which said B-mode image is displayed on a screen of a television set or cathode ray oscilloscope.

10. A method as defined in claim 1, including the additional step of performing a Doppler frequency shift measurement in respect of fluid flowing through said vessel, and using the established orientation and cross-sectional dimensions of said vessel to calculate the flow rate of said fluid.

11. Apparatus for establishing the orientation and cross-sectional dimensions of a vessel having an axis, said apparatus comprising:
(a) conventional apparatus for generating a beam of ultrasonic energy and scanning said beam over at least part of said vessel, to obtain a B-mode ultrasonic echogram image of said vessel or part thereof from a number of A-mode ultrasonic images, each corresponding to a respective A-mode line of sight of said beam;
(b) operator-activated means for establishing an angle marker in the form of a short line segment within or close to the B-mode image of said vessel or part thereof;
(c) accumulation means for accumulating echoes relating to respective sub-sectors of a plurality of sub-sectors of said B-mode image, said sub-sectors (i) being adjacent to each other, (ii) being intersected by said angle marker, and (iii) containing substantially equal numbers of adjacent A-mode lines of sight of said scanning beam;
(d) averaging means for producing a respective average A-mode signal for each of said sub-sectors;
(e) comparison means for comparing said average A-mode signals and for obtaining differences between the average A-mode signals, to enable the orientation of said axis relative to said angle marker to be computed;
(f) combining means for combining said average A-mode signals to produce a composite A-mode signal; and
(g) analytical means to perform edge analysis on said composite A-mode signal and to obtain therefrom a value of the diameter of said vessel or part thereof.

12. Apparatus as defined in claim 11, in which said accumulation means, averaging means, comparison means, combining means and analytical means are constituted by a single computer programmed to sequentially perform the functions of said accumulation means, averaging means, comparison means, combining means and analytical means.

13. Apparatus as defined in claim 12, including Doppler frequency shift measuring means for measuring the Doppler frequency shift of ultrasonic signals due to the flow of liquid through said vessel.

14. Apparatus as defined in claim 11, including a screen for display of said B-mode echogram image.

15. Apparatus as defined in claim 11, including Doppler frequency shift measuring means for measuring the Doppler frequency shift of ultrasonic signals due to the flow of liquid through said vessel.

* * * * *